US012797153B2

(12) United States Patent
Blue et al.

(10) Patent No.: US 12,797,153 B2
(45) Date of Patent: Nov. 17, 2026

(54) SYSTEMS AND METHODS FOR ORTHOGONAL INTRAVENTRICULAR ACCESS

(71) Applicant: THE TRUSTEES OF THE UNIVERSITY OF PENNSYLVANIA, Philadelphia, PA (US)

(72) Inventors: Rachel Blue, Philadelphia, PA (US); Michael Spadola, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 453 days.

(21) Appl. No.: 18/494,872

(22) Filed: Oct. 26, 2023

(65) Prior Publication Data

US 2024/0050186 A1 Feb. 15, 2024

Related U.S. Application Data

(63) Continuation of application No. PCT/US2022/026951, filed on Apr. 29, 2022.

(Continued)

(51) Int. Cl.

*A61B 90/10* (2016.01)
*A61B 90/11* (2016.01)

(Continued)

(52) U.S. Cl.

CPC .............. *A61B 90/10* (2016.02); *A61B 90/11* (2016.02); *A61M 25/02* (2013.01);

(Continued)

(58) Field of Classification Search

CPC . A61B 90/10; A61B 90/11; A61B 2090/0813; A61B 2090/103;

(Continued)

(56) References Cited

U.S. PATENT DOCUMENTS

| | | | |
|---|---|---|---|
| 10,632,283 | B2 | 4/2020 | Withers |
| 2014/0324024 | A1 | 10/2014 | Tejani |

(Continued)

FOREIGN PATENT DOCUMENTS

| | | | |
|---|---|---|---|
| CN | 202223730 | U | 5/2012 |
| WO | WO 2017/031340 | A1 | 2/2017 |

(Continued)

OTHER PUBLICATIONS

English translation Chinese Patent Publication No. CN 202223730 U (2012).*

(Continued)

*Primary Examiner* — John Kim
(74) *Attorney, Agent, or Firm* — Baker Botts LLP

(57) ABSTRACT

Devices and methods for stereotactic placement of a catheter are disclosed herein. The device can include a conical component comprising a first opening and a second opening, a cylindrical rod for receiving the catheter, a footplate for securing the device underneath a skin of a subject, and a clip for holding the catheter. The first opening and second opening can form a lumen therethrough. The cylindrical rod can be coupled to the first opening, and the footplate can be coupled to the conical component.

18 Claims, 7 Drawing Sheets

Related U.S. Application Data

(60) Provisional application No. 63/182,229, filed on Apr. 30, 2021.

(51) Int. Cl.

| | |
|---|---|
| ***A61M 25/02*** | (2006.01) |
| ***A61M 39/02*** | (2006.01) |
| *A61B 90/00* | (2016.01) |
| *A61M 25/00* | (2006.01) |
| *B33Y 80/00* | (2015.01) |

(52) U.S. Cl.

CPC . *A61M 39/0247* (2013.01); *A61B 2090/0813* (2016.02); *A61B 2090/103* (2016.02); *A61M 25/0097* (2013.01); *A61M 2025/0213* (2013.01); *A61M 2025/024* (2013.01); *A61M 2025/028* (2013.01); *A61M 2039/025* (2013.01); *A61M 2039/0258* (2013.01); *A61M 2039/0261* (2013.01); *A61M 2039/0267* (2013.01); *A61M 2039/0273* (2013.01); *A61M 2039/0282* (2013.01); *B33Y 80/00* (2014.12)

(58) Field of Classification Search

CPC .............. A61M 25/0097; A61M 25/02; A61M 39/0247; A61M 2025/0213; A61M 2025/024; A61M 2025/028; A61M 2039/025; A61M 2039/0258; A61M 2039/0261; A61M 2039/0267; A61M 2039/0273; A61M 2039/0282; B33Y 80/00

See application file for complete search history.

(56) References Cited

U.S. PATENT DOCUMENTS

| | | | | |
|---|---|---|---|---|
| 2015/0119753 | A1* | 4/2015 | Cosgrove ............. | A61B 5/4064 600/562 |
| 2015/0343709 | A1 | 12/2015 | Gerstle et al. | |
| 2017/0340864 | A1 | 11/2017 | Rios et al. | |

FOREIGN PATENT DOCUMENTS

| | | | |
|---|---|---|---|
| WO | WO 2017/174851 | A1 | 10/2017 |
| WO | WO 2020/248067 | A1 | 12/2020 |

OTHER PUBLICATIONS

Extended European Search Report dated Feb. 10, 2025 in Application No. EP 22796812.

International Search Report mailed Jul. 13, 2022 in International Application No. PCT/US2022/026951.

* cited by examiner

SYSTEMS AND METHODS FOR ORTHOGONAL INTRAVENTRICULAR ACCESS

CROSS-REFERENCE TO RELATED APPLICATIONS

This application is a continuation of International Patent Application No. PCT/US2022/026951, filed on Apr. 29, 2022, which claims priority to U.S. Provisional Application Ser. No. 63/182,229, filed on Apr. 30, 2021, the contents of which are incorporated by reference herein in their entireties.

BACKGROUND

Safe and reliable access to the ventricular system is important for successful neurosurgery. In the operating room, access to the ventricular system can be achieved by way of internal ventricular shunts. For example, extra ventricular drainage (EVD) is a common neurosurgical procedure often performed under emergent conditions at the bedside. Certain techniques can be used to place a catheter into the ipsilateral frontal horn for EVD. For example, a catheter can be placed at Kocher's point (i.e., 2-3 centimeters lateral to the midline and 11 centimeters posterior to the nasion) in the trajectory of the ipsilateral medial canthus, and the tragus can cannulate the anterior lateral ventricle, given normal ventricular and calvarial anatomy. Furthermore, placement of a catheter at Kocher's point directed in a trajectory at a right angle (orthogonal) to the cranial surface can cannulate the anterior lateral ventricle, given normal ventricular and calvarial anatomy. Even though certain freehand techniques using superficial anatomical landmarks (e.g., medial canthus and tragus) can be used for EVD placement, the accuracy rate of EVD catheter placement can be from 39.9% to 84%, demonstrating a need for improvement. Finding an accurate trajectory can be challenging under bedside conditions without pinning of the head and control of general anesthesia. Accordingly, there remains a need for an improved technique for orthogonal intraventricular access.

SUMMARY

The disclosed subject matter provides devices and methods for stereotactic placement of a catheter.

An example device can include a conical component comprising a first opening and a second opening, a cylindrical rod for receiving the catheter, a footplate for securing the device underneath a skin of a subject, and a clip for holding the catheter. The first opening and second opening can form a lumen therethrough. The cylindrical rod can be coupled to the first opening, and the footplate can be coupled to the conical component.

In certain embodiments, the conical component can be a 180-degree hollow truncated conical component. The second opening can be located at a base of the conical component, and the base can be configured to contact a target tissue. In non-limiting embodiments, the target tissue can be a calvarial surface anterior to a burr hole. The diameter of the second opening can be from about 0.5 cm to about 1.5 cm. The first opening can be located at a top of the conical component. The diameter of the first opening can be from about 0.25 cm to about 0.75 cm. In non-limiting embodiments, the height of the conical component can be about 1 cm.

In certain embodiments, the footplate can be configured to be located at a calvarial surface anterior to a burr hole to secure the device underneath a skin of a subject. The length of the footplate can be from about 0.1 cm to about 2 cm.

In certain embodiments, a portion of the cylindrical rod can be located in the lumen. The diameter of the cylindrical rod can be from about 0.1 cm to about 0.75 cm. In certain embodiments, the cylindrical rod can include a lumen that can be configured to receive a catheter so that the catheter can be aligned parallel to the cylindrical rod and placed through a frustum of the conical component into a ventricle.

In certain embodiments, the clip can be configured to hold a catheter in place during a surgical procedure.

In certain embodiments, the device can be configured to be placed on the calvarial surface anterior to a burr hole in a semi-circular way so that an entire burr hole is free for catheter placement.

The disclosed subject matter provides methods for placing a catheter. An example method can include placing a device on a target hole for inserting the catheter, wherein the device can include a conical component comprising a first opening and a second opening, a cylindrical rod for receiving the catheter, a footplate for securing the device underneath of a skin of a subject, and a clip for holding the catheter. The first opening and second opening can form a lumen therethrough. The cylindrical rod can be coupled to the first opening, and the footplate can be coupled to the conical component. The method can further include aligning the catheter parallel to the cylindrical rod and placing the catheter through a frustum of the conical component into a target tissue.

In certain embodiments, the method can further include holding the catheter using the clip during a surgical procedure. In non-limiting embodiments, the device can be printed using a three-dimensional printer.

In certain embodiments, the subject shows an indication. The indication can include subarachnoid hemorrhage, intraventricular hemorrhage, traumatic brain injury (TBI), hydrocephalus, pseudotumor and post-surgical wound drainage, or a combination thereof.

BRIEF DESCRIPTION OF THE DRAWINGS

Further features and advantages of the present disclosure will become apparent from the following detailed description taken in conjunction with the accompanying FIGS. showing illustrative embodiments of the present disclosure, in which.

Throughout the figures, unless otherwise stated, are used to denote like features, elements, components, or portions of the illustrated embodiments. Moreover, while the present disclosure will now be described in detail with reference to the figures, it is done so in connection with the illustrative embodiments.

DETAILED DESCRIPTION

The disclosed subject matter relates to devices and methods for stereotactic placement of catheters. The disclosed subject matter can be used with moderate or local sedation without the use of general anesthesia.

Unless otherwise defined, all technical and scientific terms used herein have the same meanings as commonly understood by one of ordinary skill in the art.

An "individual," "patient," or "subject," as used interchangeably herein, can be a human or non-human animal. Non-limiting examples of non-human animal subjects include non-human primates, dogs, cats, mice, rats, guinea pigs, rabbits, pigs, fowl, horses, cows, goats, sheep, and cetaceans.

The term "about" or "approximately" means within an acceptable error range for the particular value as determined by one of ordinary skill in the art, which will depend, in part, on how the value is measured or determined, i.e., the limitations of the measurement system. For example, "about" can mean within 3 or more than 3 standard deviations, per the practice in the art. Alternatively, "about" can mean a range of up to +/−20%, up to +/−10%, up to +/−5%, and up to +/−1% of a given value. Alternatively, particularly with respect to biological systems or processes, the term can mean within an order of magnitude, e.g., within 5-fold or within 2-fold, of a value.

The term "coupled," as used herein, refers to the connection of a device component to another device component by any means known in the art. The type of coupling used to connect two or more device components can depend on the scale and operability of the device. For example, and not by way of limitation, a coupling of two or more components of a device disclosed herein can include one or more joints, valves, fittings, couplings, transfer lines, or sealing elements.

Figure 1B:
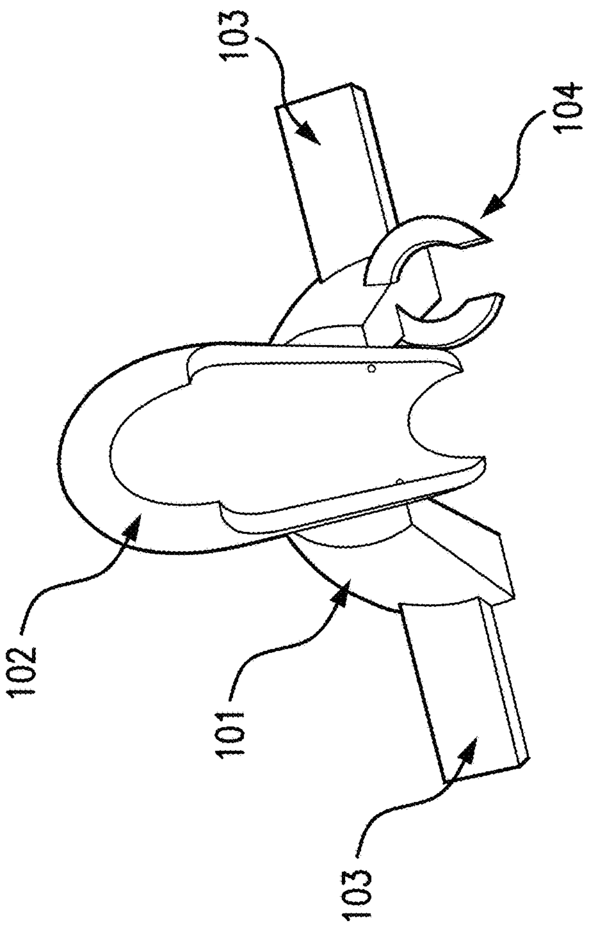
FIG. 1B is an illustration of a top view of an exemplary device in accordance with the present disclosure.
Figure 1A:
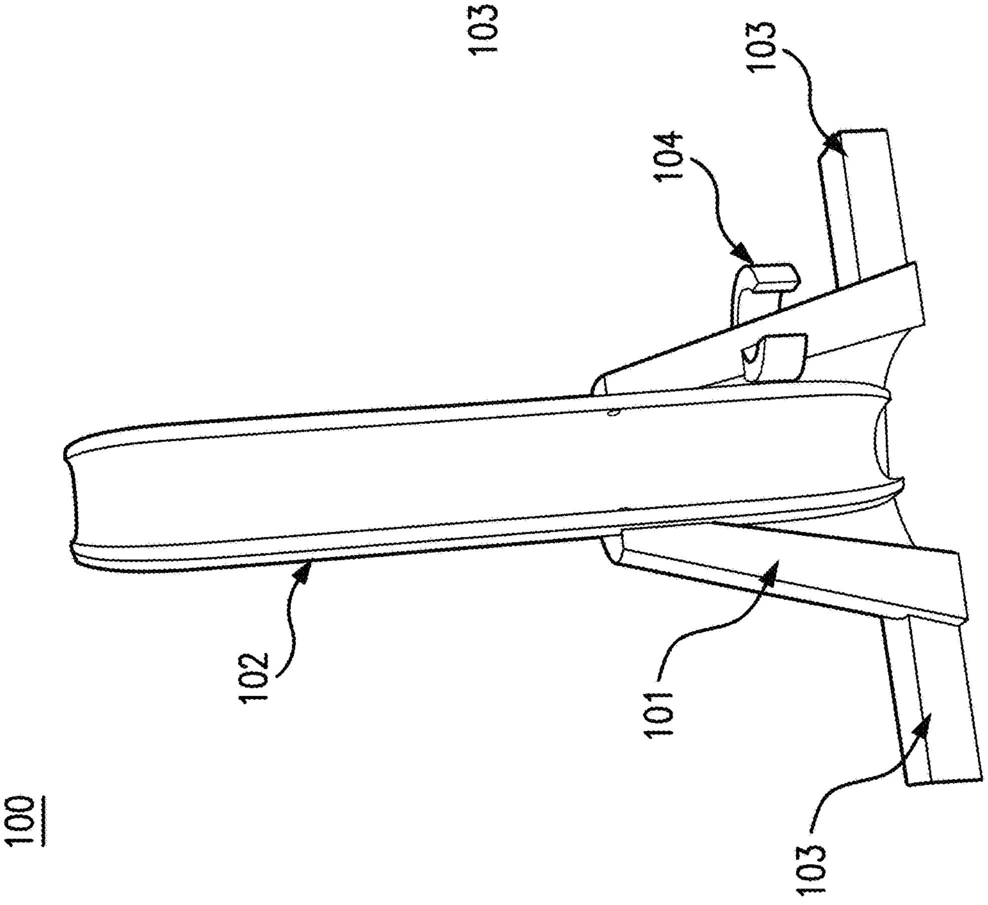
FIG. 1A is an illustration of a front view of an exemplary device in accordance with the present disclosure.

In certain embodiments, the disclosed subject matter provides a device for stereotactic placement of catheters. For example, the disclosed device can be used by surgeons to gain intraventricular access for drains and shunts. In non-limiting embodiments, the disclosed device can be used as a stand-alone adjunct for ventricular catheter navigation. As shown in FIGS. 1A and 1B, an exemplary device 100 can include a conical 101, a cylindrical rod 102, a footplate 103, and a clip 104.

Figure 2B:
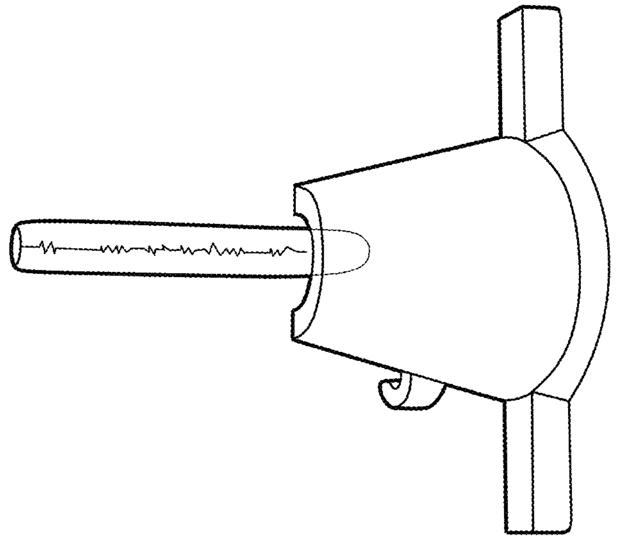
FIG. 2B is a photo image of a back view of an exemplary device with a cylindrical rod coupled to a conical component in accordance with the present disclosure.
Figure 2A:
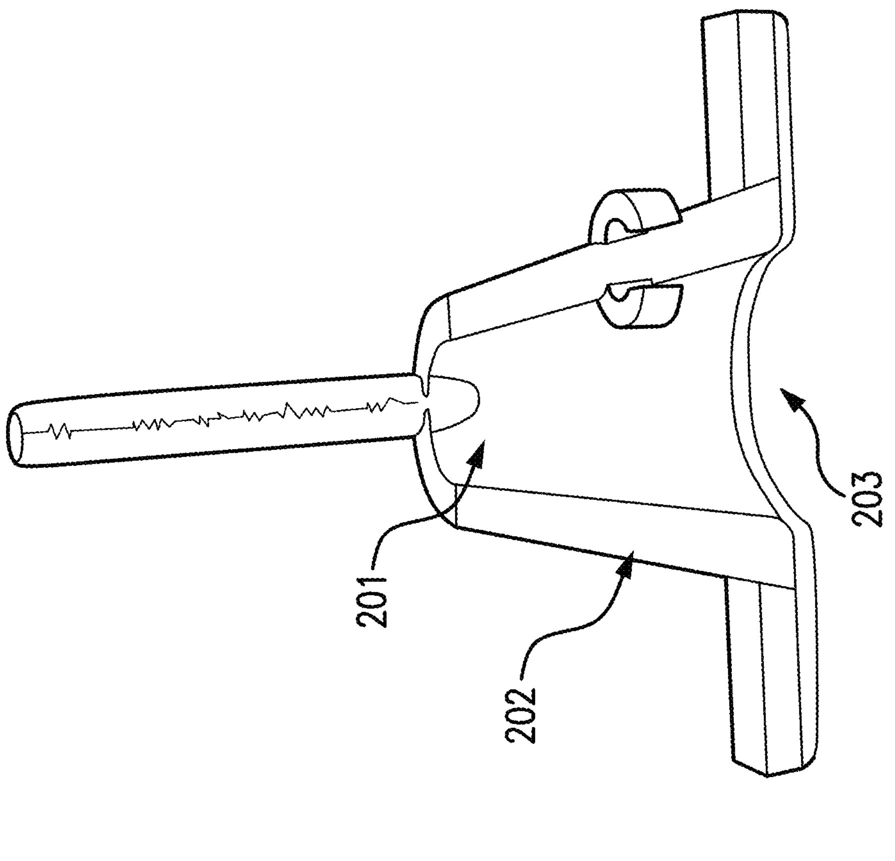
FIG. 2A is a photo image of a front view of an exemplary device with a cylindrical rod coupled to a conical component in accordance with the present disclosure.

In certain embodiments, the conical component can include a first opening and a second opening that form a lumen therethrough. As shown in FIG. 2A, the first opening 201 can be located on the top of the conical component 202. In non-limiting embodiments, the diameter of the first opening can be from about 0.01 cm to about 1 cm, from about 0.01 cm to about 0.9 cm, from about 0.01 cm to about 0.8 cm, from about 0.01 cm to about 0.75 cm, from about 0.02 cm to about 0.75 cm, from about 0.03 cm to about 0.75 cm, from about 0.04 cm to about 0.75 cm, from about 0.05 cm to about 0.75 cm, from about 0.06 cm to about 0.75 cm, from about 0.07 cm to about 0.75 cm, from about 0.08 cm to about 0.75 cm, from about 0.09 cm to about 0.75 cm, from about 0.1 cm to about 0.75 cm, from about 0.2 cm to about 0.75 cm, from about 0.25 cm to about 0.75 cm, from about 0.3 cm to about 0.75 cm, from about 0.4 cm to about 0.75 cm, or from about 0.5 cm to about 0.75 cm. The size of the first opening can vary depending on the size of the catheter. In non-limiting embodiments, the cylindrical rod can be coupled to the first opening (FIGS. 2A and 2B). As shown in FIG. 2A, the second opening 203 can be located on the base of the conical component 202. In non-limiting embodiments, the diameter of the second opening can be from about 0.01 cm to about 2 cm, from about 0.01 cm to about 1.9 cm, from about 0.01 cm to about 1.8 cm, from about 0.01 cm to about 1.7 cm, from about 0.01 cm to about 1.6 cm, from about 0.01 cm to about 1.5 cm, from about 0.05 cm to about 1.5 cm, from about 0.03 cm to about 1.5 cm, from about 0.04 cm to about 1.5 cm, from about 0.05 cm to about 1.5 cm, from about 0.06 cm to about 1.5 cm, from about 0.07 cm to about 1.5 cm, from about 0.08 cm to about 1.5 cm, from about 0.09 cm to about 1.5 cm, from about 0.1 cm to about 1.0 cm, from about 0.1 cm to about 1.5 cm, from about 0.2 cm to about 1.5 cm, from about 0.3 cm to about 1.5 cm, from about 0.4 cm to about 1.5 cm, from about 0.5 cm to about 1.5 cm, from about 0.6 cm to about 1.5 cm, from about 0.7 cm to about 1.5 cm, from about 0.8 cm to about 1.5 cm, from about 0.9 cm to about 1.5 cm, or from about 1 cm to about 1.5 cm.

In certain embodiments, the thickness of the wall of the conical component can be from about 0.01 cm to about 3 cm, from about 0.02 cm to about 3 cm, from about 0.05 cm to about 3 cm, from about 0.1 cm to about 3 cm, from about 0.1 cm to about 2.5 cm, from about 0.1 cm to about 2 cm, from about 0.01 cm to about 1.5 cm, or about from about 0.01 cm to about 1 cm.

In certain embodiments, the base of the conical component can be configured to contact a target area. For example, the base of the conical component can be contacted with or be located on a calvarial surface anterior to a burr hole. In non-limiting embodiments, the first opening and the second opening can form a hollow lumen through which a user can view the burrhole. In non-limiting embodiments, the size of the openings can be varied as long as the burrhole lies at the midpoint of the conical base.

In certain embodiments, the conical component can be configured to be placed on the calvarial surface anterior to the burrhole in a semi-circular fashion, leaving the entire burrhole free for catheter placement. For example, as shown in FIGS. 1A and 2A, the conical component can be a 180-degree hollow truncated conical component. In non-limiting embodiments, the height of the conical component can be at least about 0.1 cm, at least about 0.2 cm, at least about 0.3 cm, at least about 0.4 cm, at least about 0.5 cm, at least about 0.6 cm, at least about 0.7 cm, at least about 0.8 cm, at least about 0.9 cm, or at least about 1 cm.

In non-limiting embodiments, the conical component can be a 180-degree hollow truncated conical component, with a diameter of about 1.5 cm at its base, which can make contact with the calvarial surface, anterior to the burrhole. The half conical component can be about 1 cm in height and about 0.75 cm in diameter at the apex. The half conical component can include a hollow lumen through which the burrhole can be observed. The disclosed measurements can be varied as long as the burrhole lies at the midpoint of the conical base.

Figure 3B:
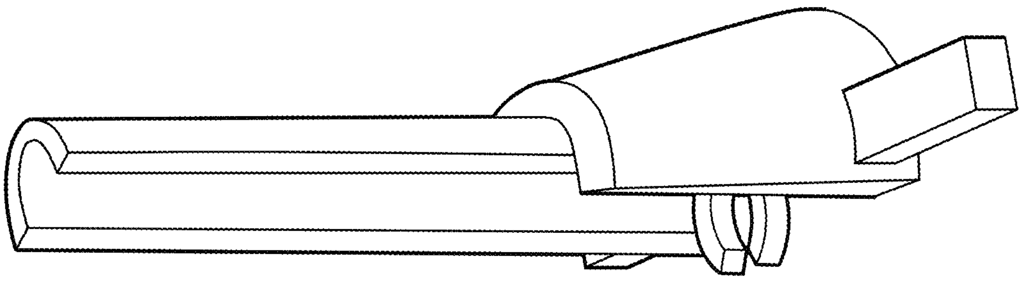
FIG. 3B is a photo image of a side view of an exemplary device with a cylindrical rod located in a lumen of a conical component in accordance with the present disclosure.
Figure 3A:
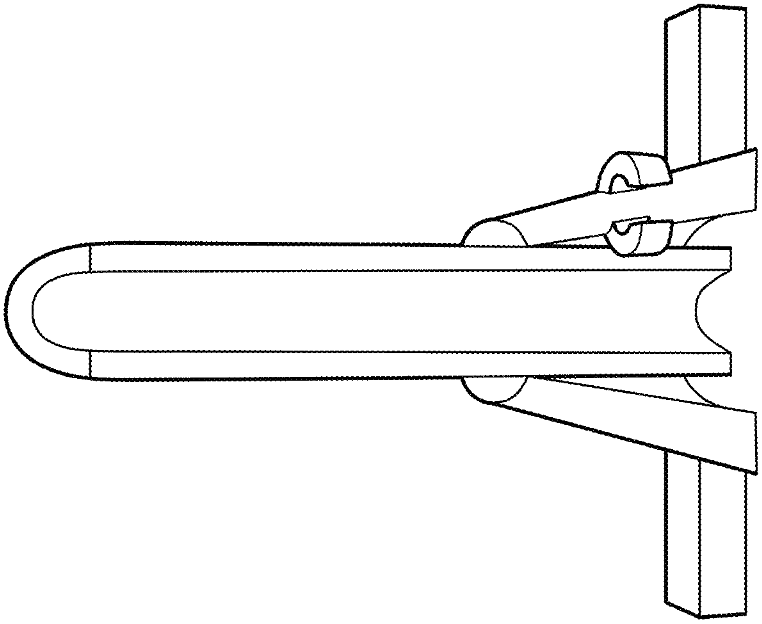
FIG. 3A is a photo image of a front view of an exemplary device with a cylindrical rod located in a lumen of a conical component in accordance with the present disclosure.

In certain embodiments, the cylindrical rod can be coupled to the conical component. For example, as shown in FIGS. 2A and 2B, the cylindrical rod can be coupled to the conical component adjacent to the first opening. The diameter of the cylindrical rod can be from about 0.01 cm to about 1 cm, from about 0.01 cm to about 0.9 cm, from about 0.01 cm to about 0.8 cm, from about 0.01 cm to about 0.75 cm, from about 0.02 cm to about 0.75 cm, from about 0.03 cm to about 0.75 cm, from about 0.04 cm to about 0.75 cm, from about 0.05 cm to about 0.75 cm, from about 0.06 cm to about 0.75 cm, from about 0.07 cm to about 0.75 cm, from about 0.08 cm to about 0.75 cm, from about 0.09 cm to about 0.75 cm, from about 0.1 cm to about 0.75 cm, from about 0.2 cm to about 0.75 cm, from about 0.25 cm to about 0.75 cm, from about 0.3 cm to about 0.75 cm, from about 0.4 cm to about 0.75 cm, pr from about 0.5 cm to about 0.75 cm. In non-limiting embodiments, the diameter of the cylindrical rod can be about 0.75 cm. In non-limiting embodiments, the length of the cylindrical rod can be from about 1 cm to about 10 cm. In non-limiting embodiments, as shown in FIGS. 1 and 3, a portion of the cylindrical rod can be located in the lumen of the conical component.

In certain embodiments, the cylindrical rod can include a lumen. The lumen of the cylindrical rod can be configured to receive a catheter. For example, the catheter can be inserted into the lumen of the cylindrical rod and be aligned parallel to the cylindrical rod. Then, the catheter can be placed through a frustum of the conical component into a ventricle.

In certain embodiments, the diameter of the lumen of the cylindrical rod can be from about 0.01 cm to about 2 cm, from 0.01 cm to about 1.5 cm, from 0.01 cm to about 1 cm, from 0.02 cm to about 1 cm, from 0.03 cm to about 1 cm, from 0.04 cm to about 1 cm, from 0.05 cm to about 1 cm, from 0.06 cm to about 1 cm, from 0.07 cm to about 1 cm, from 0.08 cm to about 1 cm, from 0.09 cm to about 1 cm, or from 0.1 cm to about 1 cm.

In certain embodiments, the length of the cylindrical rod can be from about 0.1 cm to about 10 cm, from about 0.1 cm to about 9 cm, from about 0.1 cm to about 8 cm, from about 0.1 cm to about 7 cm, from about 0.1 cm to about 6 cm, from about 0.1 cm to about 5 cm, from about 0.2 cm to about 5 cm, from about 0.3 cm to about 5 cm, from about 0.4 cm to about 5 cm, from about 0.5 cm to about 5 cm, from about 0.6 cm to about 5 cm, from about 0.7 cm to about 5 cm, from about 0.8 cm to about 5 cm, from about 0.9 cm to about 5 cm, about 1.0 cm to 5.0 cm, about 1.0 cm to 4.0 cm, or about 1.0 cm to 3.0 cm.

Figure 4B:
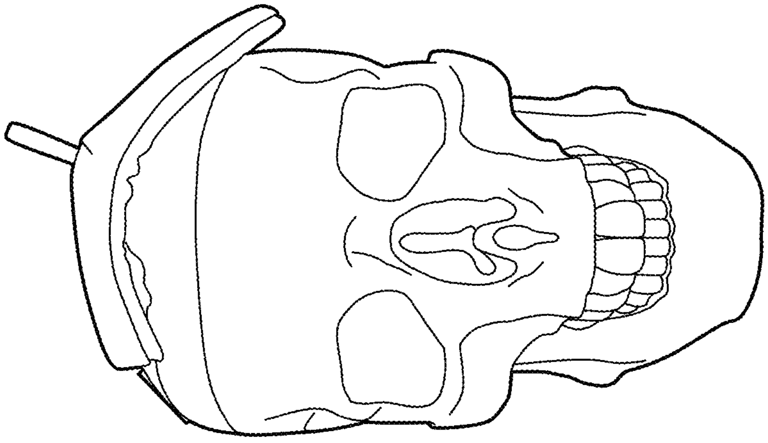
FIG. 4B is a photo image of a front view of a skull model with an exemplary device implanted under the skin in accordance with the present disclosure
Figure 4A:
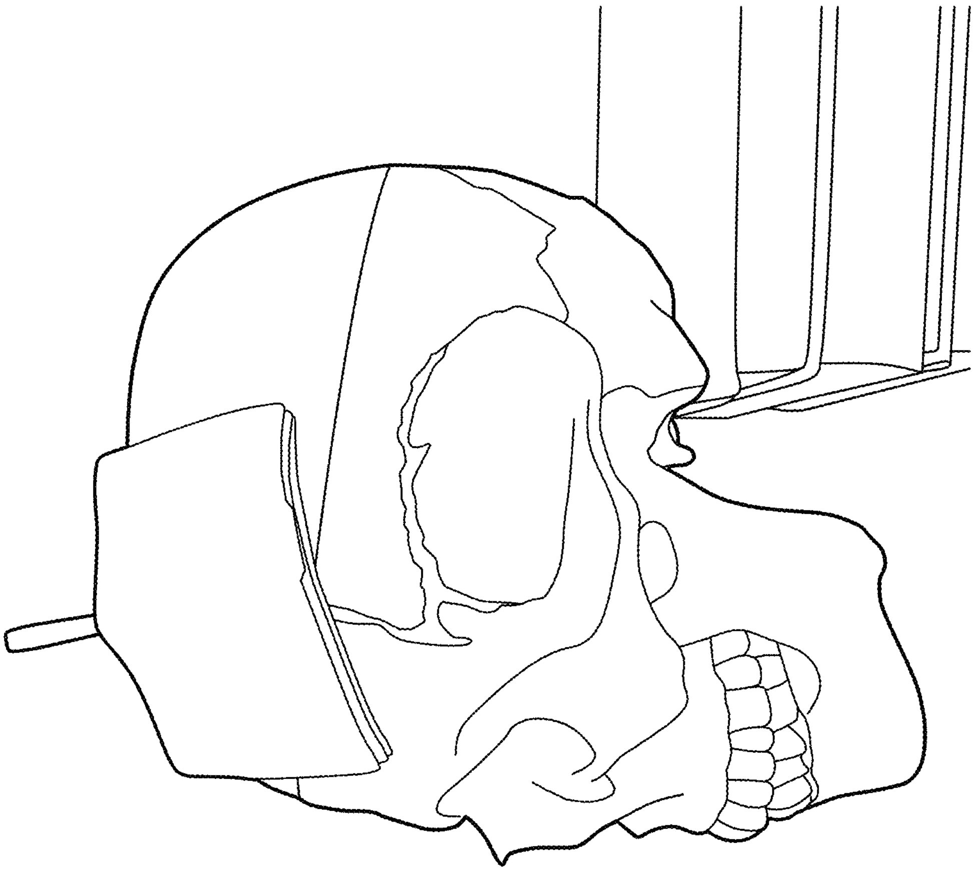
FIG. 4A is a photo image of a side view of a skull model with an exemplary device implanted under the skin in accordance with the present disclosure.

In certain embodiments, the footplate can be coupled to the conical component. In non-limiting embodiments, the footplate can be coupled to the base of the conical component for securing the position of the disclosed device. For example, as shown in FIGS. 4A and 4B, the footplate can be configured to be located at a calvarial surface anterior to a burr hole to secure the device underneath a skin of a subject. In non-limiting embodiments, the length of the footplate can be about from 0.1 cm to about 2 cm, from 0.1 cm to about 1.75 cm, from 0.1 cm to about 1.5 cm, from 0.1 cm to about 1 cm, from 0.2 cm to about 1 cm, from 0.3 cm to about 1 cm, from 0.4 cm to about 1 cm, or from 0.5 cm to about 1 cm.

In certain embodiments, the clip can be coupled to the conical component. As shown in FIGS. 1-3, the clip 104 can be coupled to the wall of the conical component 101. The clip can be configured to hold a catheter in place during a surgical procedure (e.g., tunneling the catheter, suturing the catheter securely to the scalp). This can allow the proceduralist to secure the catheter to the device so they do not have to physically hold it into place while completing the rest of the procedure. This enables the catheter to stay at the right position in the ventricle and not inadvertently fall deeper or be pulled out.

In certain embodiments, the inner diameter of the clip can be from 0.1 cm to about 1 cm, from 0.2 cm to about 1 cm, from 0.2 cm to about 0.9 cm, from 0.2 cm to about 0.8 cm, or from 0.2 cm to about 0.7 cm. In non-limiting embodiments, the outer diameter of the clip can be from about 0.2 cm to about 2 cm, from about 0.3 cm to about 2 cm, from about 0.3 cm to about 1.5 cm, from about 0.3 cm to about 1 cm, from about 0.3 cm to about 0.9 cm, or from about 0.3 cm to about 0.8 cm. In some embodiments, the height of the clip can be from 0.1 cm to about 3 cm, 0.1 cm to about 2 cm, or 0.1 cm to about 1 cm.

In certain embodiments, the disclosed comical component, the cylindrical rod, footplate, and the clip can include autoclavable resin, plastic, or any sterilizable materials. In non-limiting embodiments, the disclosed device, including the plastic, can be autoclaved for sterility. The use of plastic can allow mass production of a cheap and disposable device. In non-limiting embodiments, each compartment or the whole device can be manufactured using a three-dimensional printer.

Figure 5:
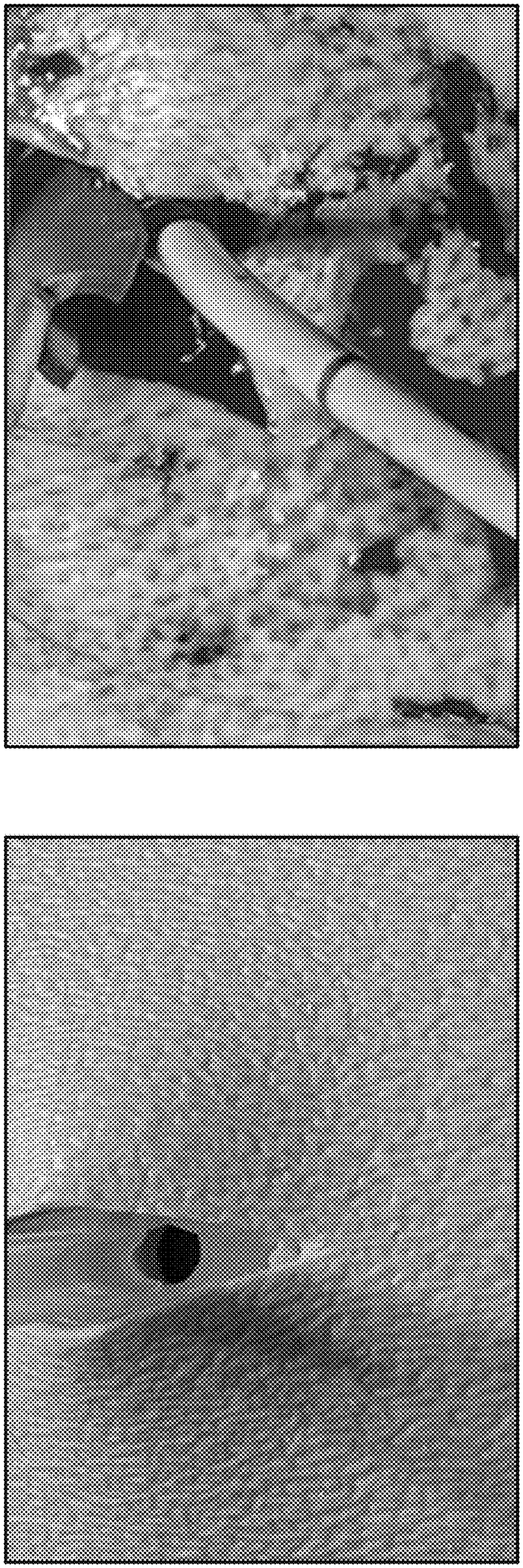
FIG. 5 is a compilation of photo images demonstrating the exemplary devices with the footplates under the skin and the conical component functioning as a skin retractor in accordance with the present disclosure.
Figure 6:
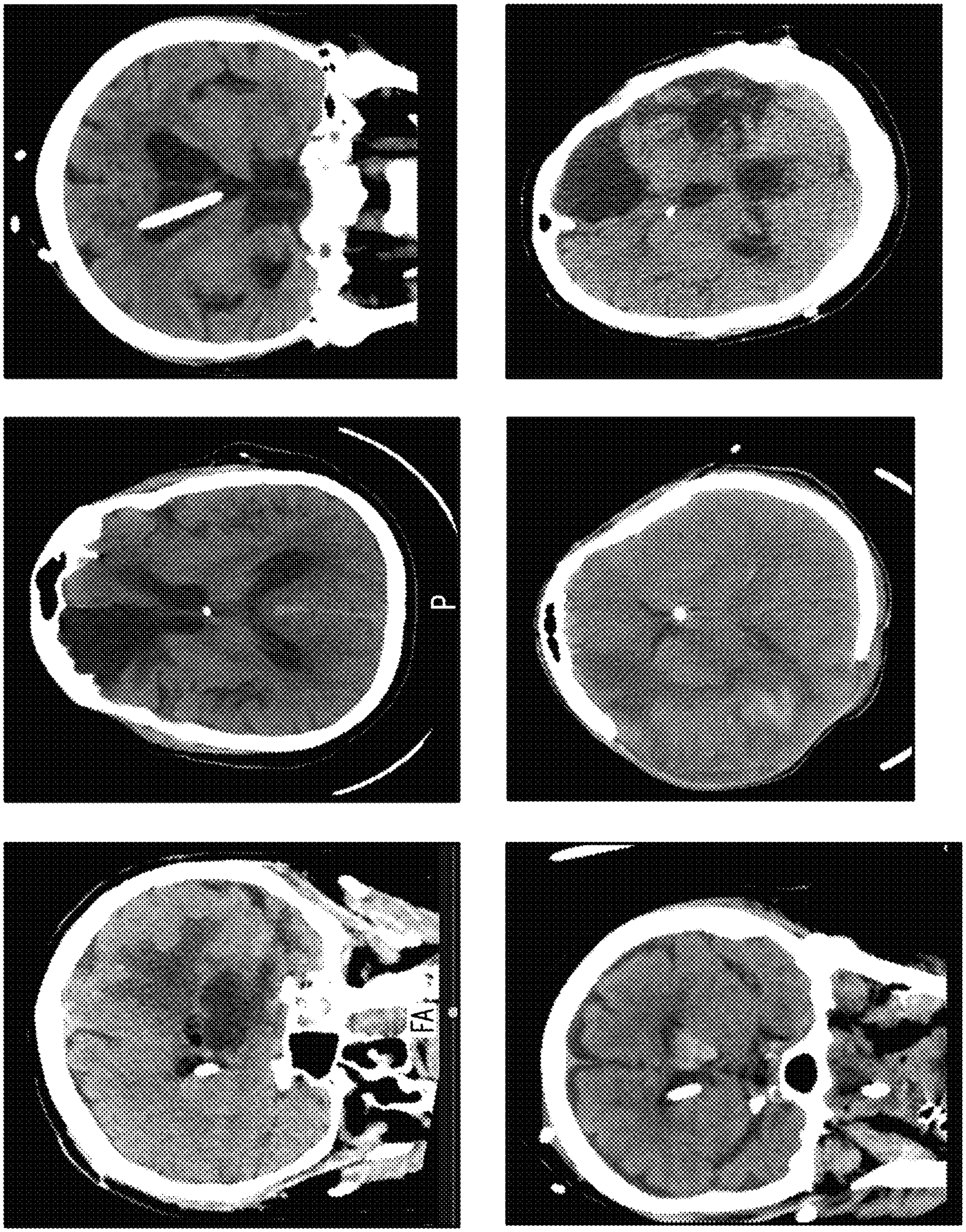
FIG. 6 demonstrates patient head computed tomography (CT) scan images demonstrating ventricular placement with the disclosed device assistance in accordance with the present disclosure.

FIG. 5 demonstrates the disclosed device in use. The footplates sit under the skin, and the conical component functions as a stand-alone skin retractor, allowing the proceduralist to have a full view of the surgical site and burrhole. FIG. 5 also demonstrates the clip in use, allowing for secure holding of the catheter so the proceduralist can have both hands free for additional parts of the procedure. FIG. 6 demonstrates head CT scans from 6 patients who underwent ventricular placement using device assistance, demonstrating successful ventricular cannulation.

Figure 7:
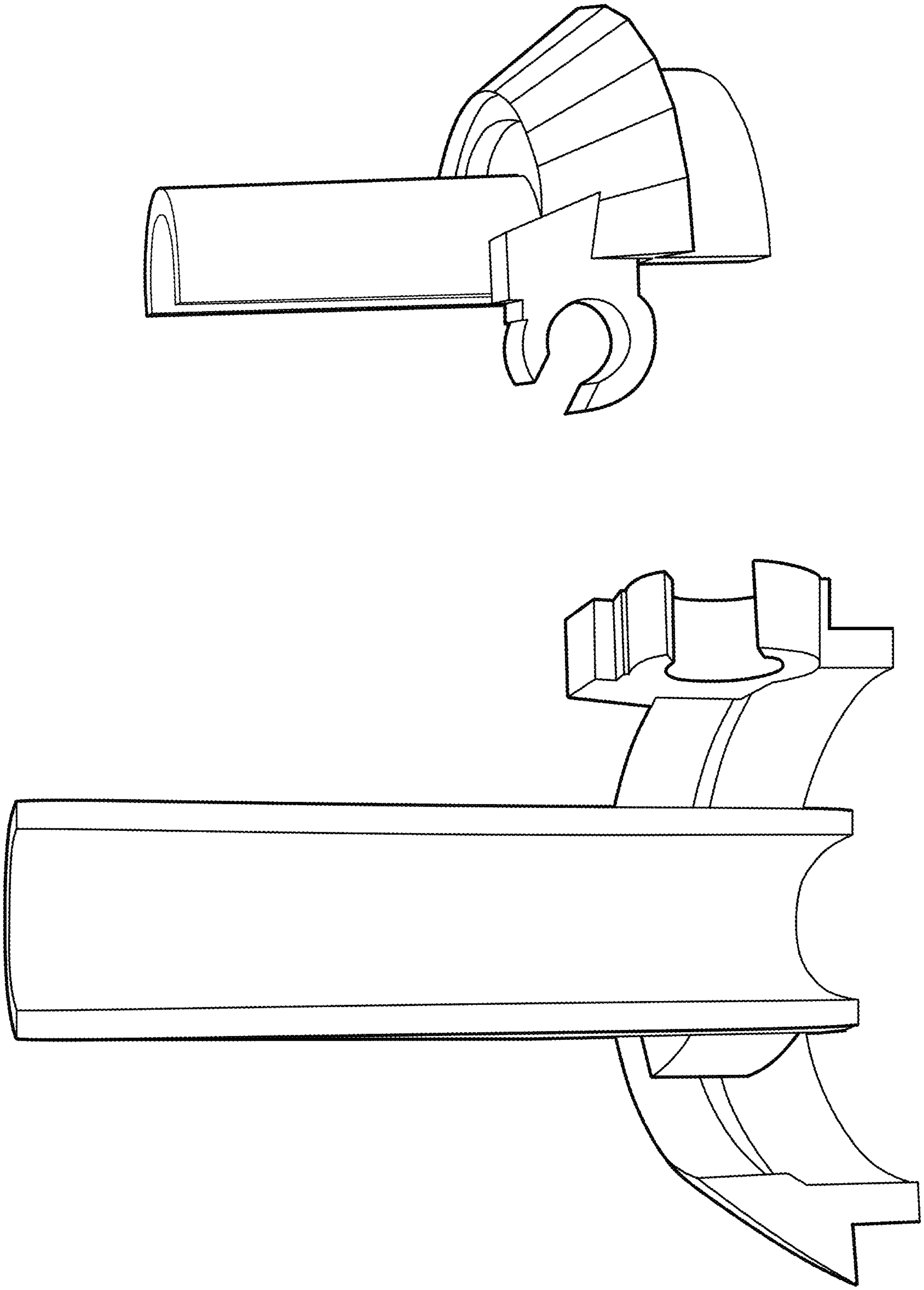
FIG. 7 is an illustration of an exemplary device with an alternative design in accordance with the present disclosure.

FIG. 7 demonstrates the disclosed device with an alternative design. The disclosed device can include a burr hole adaptor to allow hand-free operation. In non-limiting embodiments, the disclosed device can include a silicone or a silicone-like material to fit snug within the burr hole and avoid bony obstructions.

In certain embodiments, the disclosed subject matter provides a method for placing a catheter using the disclosed device. An example method can include placing the disclosed device on a target burrhole for inserting the catheter, aligning the catheter parallel to the cylindrical rod, and placing the catheter through a frustum of the conical component into a target tissue. In non-limiting embodiments, the method can further include holding the catheter using the clip during a surgical procedure.

In certain embodiments, the disclosed device can increase the accuracy of external ventricular drain (EVD)/shunt catheter placement allowing for less malpositioned catheters. In non-limiting embodiments, the disclosed device can be a disposal device and/or an autoclavable device so that the infection during a surgical procedure can decrease.

In non-limiting embodiments, the disclosed device can include a footprint to be used in bedside procedures without extending incision. In non-limiting embodiments, the disclosed device can allow for improved two-handed surgeon ergonomics. The disclosed device can allow the trajectory modification without locking down the user trajectory. The footplates sit under the skin holding the base of the conical component flush with the calvarial surface without having to be held in place by the proceduralist. Additionally, the clip allows for the catheter to be held in place securely prior to final securement by tunneling and suture.

In certain embodiments, the disclosed device can be used for a subject with various indications. For example, the indication can include subarachnoid hemorrhage, intraventricular hemorrhage, traumatic brain injury (TBI), hydrocephalus, pseudotumor and post-surgical wound drainage, or a combination thereof. In non-limiting embodiments, the disclosed device can provide reliable and accurate ventricular access with no clinical complications (e.g., tract hemorrhages or post-procedural infections).

In certain embodiments, the disclosed device can be used as a stand-alone adjunct for ventricular catheter navigation. In non-limiting embodiments, the disclosed subject matter provides a kit for extra-ventricular puncture/drainage or ventricular shunting systems, including the disclosed device. The disclosed subject matter can be used by neurosurgeons or other providers accessing the ventricular system that can be used at the bedside and in the operation room.

In certain embodiments, the disclosed device can allow the adjustment based on the patient's scan. For example, when the patient's scan demonstrates the shift of the ventricles based on the measurement of the pre-procedure CT scan, the proceduralist is able to adjust the angle of the catheter accordingly. In this instance, the catheter can be aligned with the trajectory demonstrated by the cylindrical component, and then the catheter angle can be adjusted slightly based on the preoperative assessment of the ventricular location.

EXAMPLES

Example 1

The effects of the disclosed subject matter on the accuracy of catheter placement were assessed by giving a ninety-degree trajectory for external ventricular drain (EVD) or shunt placement with the disclosed device. The disclosed device (i.e., DIVE guide) was sterilized and placed on the top of the skull as a guide that shows a 90-degree angle between the skull to the ventricles, which can be used for catheter placement. The device was placed without going inside the skull, brain, or ventricular system.

16 total patients have been enrolled for ventricular access using the DIVE guide. 7 patients underwent ventriculoperitoneal shunting, and 9 patients underwent bedside extraventricular drain placement. 100% (16/16) of procedures had successful ventricular cannulation in an average of 1.12 passes with 0% (0/0) requiring repositioning following confirmatory head computed tomography (HCT). On post-procedure head CT, the tip of the catheter was located in the ipsilateral frontal horn or 3rd ventricle in 87.5% (14/16) of patients and in the contralateral lateral ventricle in 12.5% (2/16) of patients. See Table 1.

TABLE 1

Effects of the DIVE guide on the accuracy of catheter placement.

| Catheter accuracy | N = 16 |
|---|---|
| Intraventricular | 100% (16/16) |
| Kakarla Grade 1 (ipsilateral frontal horn/3$^{rd}$) | 87.5% (14/16) |
| Kakarla Grade 2 (contralateral frontal horn) | 12.5% (2/16) |
| Kakarla Grade 3 (eloquent tissue/cisterns) | 0% (0/16) |

Compared to the standard freehand ventricular access, the DIVE guided procedures are superior in both the average number of passes and accuracy of catheter placement. The device clip secured the catheter during tunneling, and no catheters were inadvertently dislodged. No patients suffered clinical complications or infection.

Example 2

Safe and reliable access to the ventricular system can be an important skill in the neurosurgical armamentarium. While the freehand technique has remained an accepted method for ventricular access, the accuracy rate of catheter placement has been reported as low as 40%, pass attempts as high as 3 per procedure, and complications between 10-40%. Certain devices have been developed to assist with catheter placement. However, these devices often prove cumbersome, necessitating a large incision, or require expensive navigation technology.

The disclosed subject matter provides a low-profile device for reliable and accurate ventricular access with improved safety, efficacy and accuracy.

A novel device for ventricular entry, the DIVE guide, was designed. 50 patients undergoing extra ventricular drain (EVD) or ventricular shunt placement were prospectively enrolled for DIVE assisted catheter placement with a non-significant risk (NSR) device designation. The primary outcome is the location of the catheter tip on post-operative CT scan and secondary outcome measures include a total number of catheter passes, clinically important tract hemorrhages and post-procedural infections.

50 total patients were prospectively enrolled for ventricular access with DIVE assistance. Indications included subarachnoid hemorrhage, intraventricular hemorrhage, TBI, hydrocephalus, pseudotumor and post-surgical wound drainage. 76% (38/50) underwent right sided catheter placement and 24% (12/20) underwent left. 100% (50/50) of procedures had successful cannulation in an average of 1.06 passes. On post-procedure head CT, the tip of the catheter was located in the ipsilateral frontal horn or 3rd ventricle (Kakarla Grade 1) in 92% (46/50) and in the contralateral lateral ventricle (Kakarla Grade 2) in 8% (4/50). See Table 2. There were no clinically significant tract hemorrhages or post procedural infections.

TABLE 2

Improved accuracy of catheter placement with the DIVE guide.

| Catheter accuracy | N = 50 |
|---|---|
| Intraventricular | 100% (50/50) |
| Kakarla Grade 1 (ipsilateral frontal horn/3rd) | 92% (46/50) |
| Kakarla Grade 2 (contralateral frontal horn) | 8% (4/50) |
| Kakarla Grade 3 (eloquent tissue/cisterns) | 0% (0/16) |

As shown in Table 2, 100% of DIVE procedures had successful ventricular cannulation, with 92% achieving Kakarla Grade 1, in an average of 1.06 passes. The DIVE provides reliable and accurate ventricular access with no clinical complications.

All patents, patent applications, publications, product descriptions, and protocols, cited in this specification are hereby incorporated by reference in their entireties. In case of a conflict in terminology, the present disclosure controls.

While it will become apparent that the subject matter herein described is well calculated to achieve the benefits and advantages set forth above, the presently disclosed subject matter is not to be limited in scope by the specific embodiments described herein. It will be appreciated that the disclosed subject matter is susceptible to modification, variation, and change without departing from the spirit thereof. Those skilled in the art will recognize or be able to ascertain using no more than routine experimentation, many equivalents to the specific embodiments described herein. Such equivalents are intended to be encompassed by the following claims.

What is claimed is:

1. A device for stereotactic placement of a catheter comprising:
- a conical component comprising a first opening and a second opening, where the first opening and second opening form a lumen therethrough;
- a cylindrical rod, coupled to the conical component, for receiving the catheter, wherein a portion of the cylindrical rod is located in the lumen of the conical component;
- a footplate, coupled to the conical component, for securing the device underneath of a skin of a subject; and
- a clip, coupled to the conical component, for holding the catheter;
- wherein the device is placed on a calvarial surface anterior to a burr hole in a semi-circular way so that the burr hole is free for catheter placement.

2. The device of claim 1, wherein the second opening is located at a base of the conical component, wherein the base is configured to contact with a target tissue.

3. The device of claim 2, wherein the target tissue is a calvarial surface anterior to the burr hole.

4. The device of claim 1, wherein a diameter of the second opening is from about 0.5 cm to about 1.5 cm.

5. The device of claim 1, wherein the conical component is a 180-degree hollow truncated conical component.

6. The device of claim 1, wherein the first opening is located at a top of the conical component, wherein a diameter of the first opening is from about 0.25 cm to about 0.75 cm.

7. The device of claim 1, wherein a height of the conical component is about 1 cm.

8. The device of claim 3, wherein the device is configured to be placed on the calvarial surface anterior to a burr hole in a semi-circular way so that an entire burrhole is free for catheter placement.

9. The device of claim 1, wherein the footplate is configured to be located at a calvarial surface anterior to a burr hole to secure the device underneath a skin of a subject.

10. The device of claim 9, wherein a length of the footplate is from about 0.1 cm to about 2 cm.

11. The device of claim 9, wherein a portion of the cylindrical rod is located in the lumen.

12. The device of claim 1, wherein a diameter of the cylindrical rod is from about 0.1 cm to about 0.75 cm.

13. The device of claim 1, wherein the cylindrical rod comprises a lumen that is configured to receive a catheter so that the catheter is aligned parallel to the cylindrical rod and placed through a frustum of the conical component into a ventricle.

14. The device of claim 1, wherein the clip is configured to hold a catheter in place during a surgical procedure.

15. A method for placing a catheter comprising:
- placing a device on a target hole for inserting the catheter, wherein the device comprises
  - a conical component comprising a first opening and a second opening, where the first opening and second opening form a lumen therethrough;
  - a cylindrical rod, coupled to the first opening, for receiving the catheter, wherein a portion of the cylindrical rod is located in the lumen of the conical component;
  - a footplate, coupled to the conical component, for securing the device underneath of a skin of a subject; and
  - a clip, coupled to the conical component, for holding the catheter;
  - wherein the device is placed on a calvarial surface anterior to a burr hole in a semi-circular way so that an entire burr hole is free for catheter placement;
- aligning the catheter parallel to the cylindrical rod; and
- placing the catheter through a frustum of the conical component into a target tissue.

16. The method of claim 15, further comprising holding the catheter using the clip during a surgical procedure.

17. The method of claim 16, wherein the device is printed using a three-dimensional printer.

18. The method of claim 15, wherein the subject shows an indication, wherein the indication comprises subarachnoid hemorrhage, intraventricular hemorrhage, traumatic brain injury (TBI), hydrocephalus, pseudotumor and post-surgical wound drainage, or a combination thereof.

* * * * *